United States Patent
Ye et al.

(10) Patent No.: US 9,642,521 B2
(45) Date of Patent: May 9, 2017

(54) AUTOMATIC PUPILLARY DISTANCE MEASUREMENT SYSTEM AND MEASURING METHOD

(71) Applicant: ULSEE INC., Taipei (TW)

(72) Inventors: Zhou Ye, Foster City, CA (US);
Sheng-Wen Jeng, Tainan (TW);
Ying-Ko Lu, Guishan Township (TW);
Shih Wei Liu, Taipei (TW)

(73) Assignee: ULSee Inc., Taipei (TW)

( * ) Notice: Subject to any disclaimer, the term of this patent is extended or adjusted under 35 U.S.C. 154(b) by 0 days.

(21) Appl. No.: 14/553,991

(22) Filed: Nov. 25, 2014

(65) Prior Publication Data

US 2015/0146169 A1 May 28, 2015

Related U.S. Application Data

(60) Provisional application No. 61/909,350, filed on Nov. 26, 2013.

(51) Int. Cl.
*A61B 3/11* (2006.01)
*A61B 3/00* (2006.01)
*A61B 3/14* (2006.01)

(52) U.S. Cl.
CPC .......... *A61B 3/111* (2013.01); *A61B 3/0025* (2013.01); *A61B 3/0033* (2013.01); *A61B 3/0083* (2013.01); *A61B 3/14* (2013.01)

(58) Field of Classification Search
CPC ......... A61B 3/11; A61B 3/111; A61B 3/0025; A61B 3/0033; A61B 3/0083; A61B 3/14

USPC .............................. 351/204, 206, 208, 246
See application file for complete search history.

(56) References Cited

U.S. PATENT DOCUMENTS

| | | | |
|---|---|---|---|
| 6,535,223 B1 * | 3/2003 | Foley | A61B 3/111 345/629 |
| 7,322,697 B2 | 1/2008 | Jojiki | |
| 8,459,792 B2 | 6/2013 | Wilson | |
| 2013/0050642 A1 * | 2/2013 | Lewis | A61B 3/113 351/204 |
| 2013/0076884 A1 | 3/2013 | Choukroun | |
| 2013/0314413 A1 * | 11/2013 | Coon | A61B 3/111 345/420 |

(Continued)

*Primary Examiner* — Jordan Schwartz
(74) *Attorney, Agent, or Firm* — Alan D. Kamrath; Kamrath IP Lawfirm, P.A.

(57) ABSTRACT

Method for automatically measuring pupillary distance includes extracting facial features of face image, a head current center indicator is shown/displayed based on facial feature extraction, elliptical frame and target center indicator are shown, a first distance between head current center indicator and target center indicator is calculated to see if below a threshold range, then allowing head current center indicator, elliptical frame and target center indicator to disappear. Card window based on facial tracking result is shown. Credit card band detection is performed to see if located within card window. Card window then disappear. Elliptical frame of moving head and target elliptical frame are shown. Elliptical frame of the moving head is aligned with the target elliptical frame and maintaining a correct head posture. If elliptical frame of moving head is aligned with target elliptical frame, then allow them to disappear from view, and performing a pupillary distance measurement.

19 Claims, 17 Drawing Sheets

(56) References Cited

U.S. PATENT DOCUMENTS

| | | | | |
|---|---|---|---|---|
| 2014/0063461 A1* | 3/2014 | Yao | A61B 3/113 | 351/210 |
| 2014/0253875 A1* | 9/2014 | Le Gallou | G02C 13/005 | 351/204 |
| 2014/0293220 A1* | 10/2014 | Kornilov | A61B 3/10 | 351/204 |
| 2015/0313468 A1* | 11/2015 | Okada | A61B 3/10 | 351/208 |
| 2016/0171596 A1* | 6/2016 | Angerbauer | G02C 13/005 | 705/27.2 |

* cited by examiner

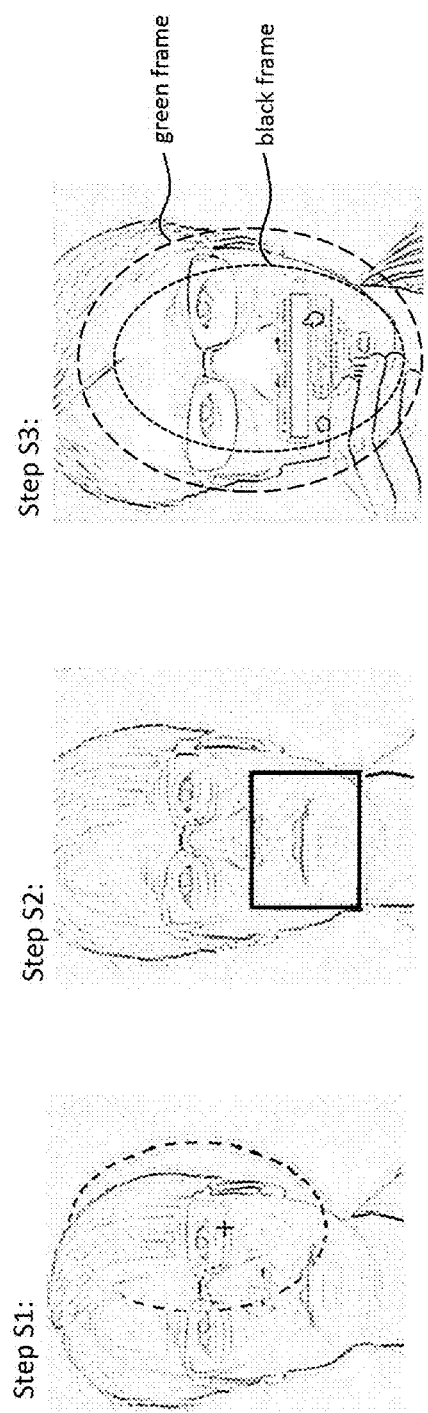

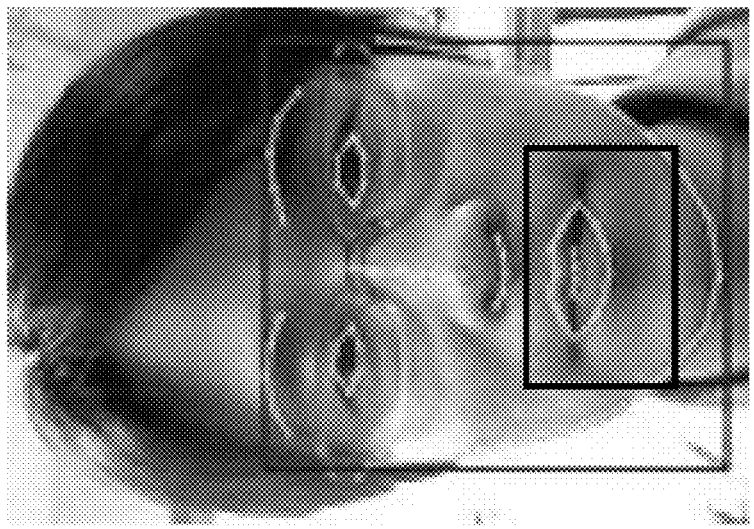
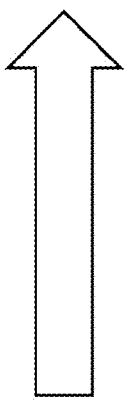
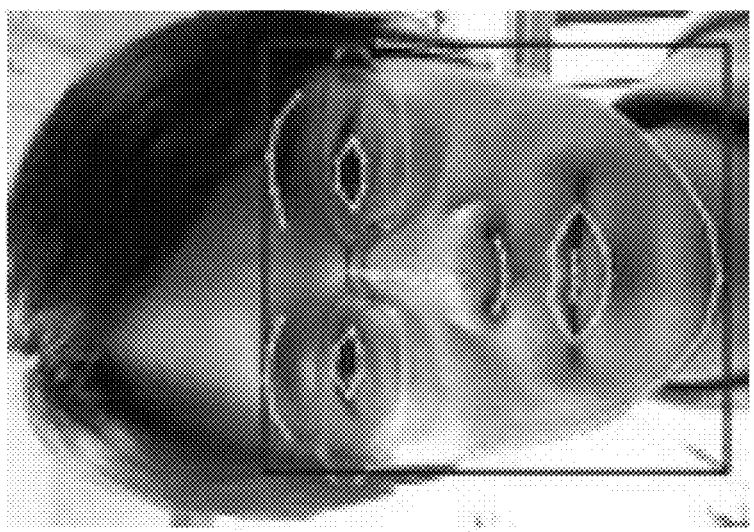
FIG. 12

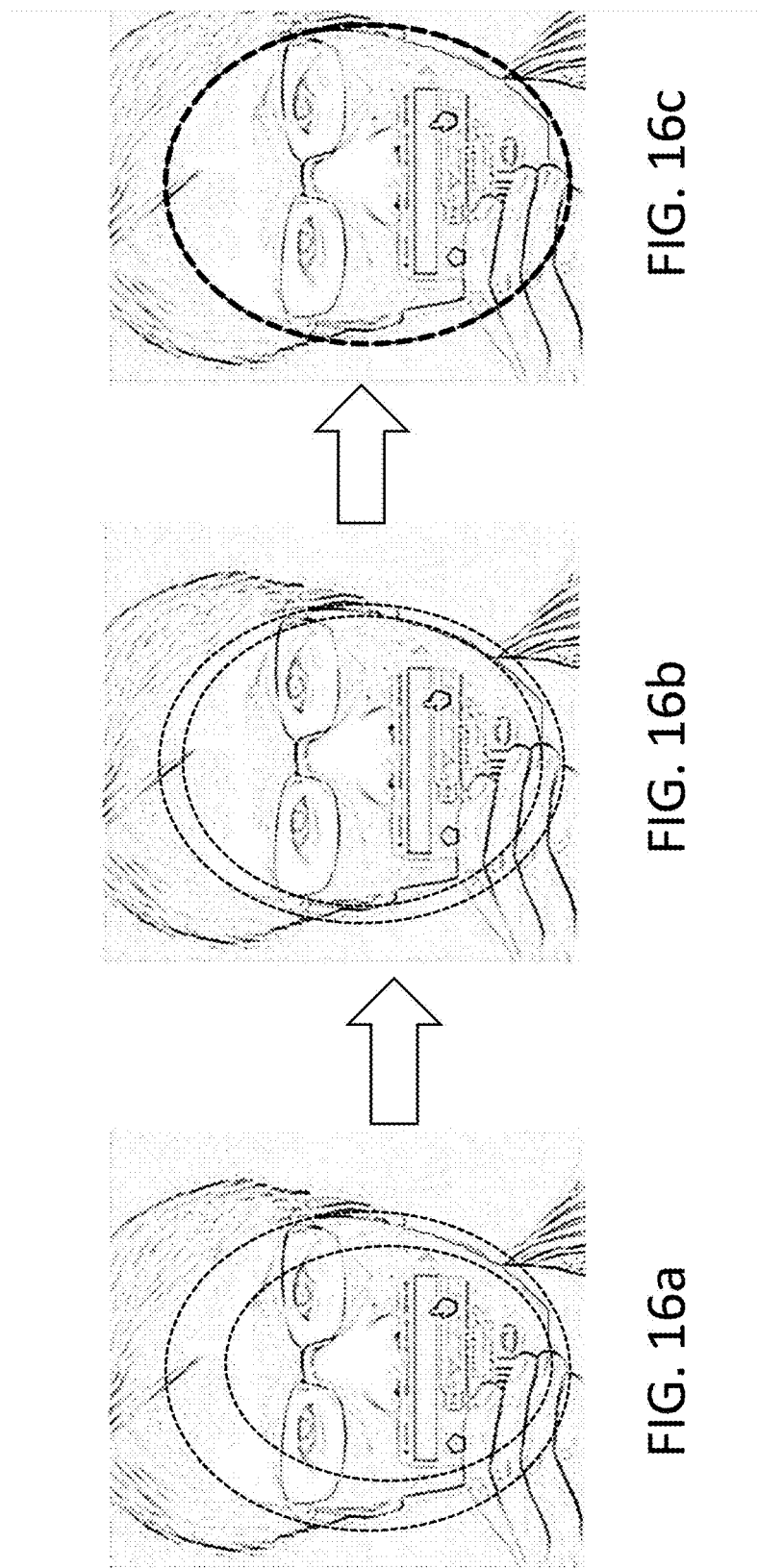

AUTOMATIC PUPILLARY DISTANCE MEASUREMENT SYSTEM AND MEASURING METHOD

CROSS-REFERENCE TO RELATED APPLICATION

This application is a non-provisional application claiming priority of U.S. provisional application No. 61/909,350, filed on Nov. 26, 2013. The entirety of the above-mentioned patent application is hereby incorporated by reference herein and made a part of this specification.

BACKGROUND OF THE INVENTION

1. Field of the Invention

The present invention generally relates to a method for automatically measuring pupillary distance (PD), and more particularly, the present invention relates to an automatic pupillary distance (PD) measurement system and a PD measuring method having capability to automatically check to detect if a measured object moves into an adequate measuring position and automatically guide the user for obtaining a correct head posture for pupillary distance (PD) measurement.

2. Description of the Related Art

Nowadays, due to the improvements in the digital technologies with the increased demand in the current marketplace for reliable automated credit card processing systems capable for handling financial transactions for customers. One possible application or usage scenario for automated credit card processing system can involve a customer purchasing a pair of glasses and paying for the purchase of the pair of glasses by holding a credit card in his hand, and directing a camera on the hand-hold device or PC for image capture of him holding the credit card, for extracting the credit card's edges as reference length (credit card has international standard width 85.6 mm) for performing a pupillary distance (PD) measurement. Meanwhile, people have recognized that automatic extraction of (eye) pupils' features and the card edges of the credit card for various users under different environments using computer vision technology today can lead to many issues and difficulties. Therefore, almost only manual vision-assisted operation systems are currently available in the marketplace today. For example, traditional manual pupillary distance (PD) measurement process includes the following steps. Step 1: As shown in FIG. 1a, a black band of the credit card undergoes adjustment by moving a mouse cursor inside a black band region of the credit card and click the mouse to identify the black band region; and visually and manually adjusting a card edge of the credit card to fit the edge of the card band in the captured photo image. Step 2: As shown in FIG. 1b, a pupil center undergoes adjustment by visually and manually moving a mouse cursor up/down to adjust an alignment frame to align with a vertical position of the pupils, and similarly, visually and manually moving the mouse cursor left/right to adjust the alignment frame to align with a horizontal position of the pupils, and then followed by obtaining a pupillary distance value. Repeatability requirement of visual detection and measurement results for the pupil distance is typically beyond manual adjustment capability (measurement error should be within 2 mm) due to contributions and influence of differences found in various human postures and operating distances relative to the camera. Therefore, the traditional manual visual detection and measurement system needs to have a smart UI to guide the user to come into or arrive at a reasonable measuring range to maintain consistent measuring condition for measuring pupil distance.

In a first usage scenario of the traditional manual pupillary distance (PD) measurement process, as shown in FIGS. 2a, 2b, and 2c, the measurement results for the pupil distance for a same user located at a same measurement distance from the camera would vary accordingly with different head postures. Therefore, even with the pupil distance being measured at the same measurement distance from the camera, the unsatisfactory or inadequate measurement accuracy of the pupil distance caused by differences in various head postures can be seen or determined. As shown in FIG. 2a, the pitch angle of the head of the person in the illustrated image is less than 0, and the pupil distance is measured to be 65.8 mm. As shown in FIG. 2b, the pitch angle of the head of the person in the illustrated image is equal to 0, and the pupil distance is measured to be 63.4 mm. Referring to FIG. 2c, the pitch angle of the head of the person in the illustrated image is greater than 0, and the pupil distance is measured to be 61.0 mm. Therefore, it is evident that at different head pitch angles, the pupil distance measurement results being obtained between 61.0 mm to 65.8 mm, are therefore not very precise or consistent.

In a second usage scenario of the traditional manual pupillary distance (PD) measurement process, as shown in FIGS. 3a, 3b, and 3c, the measurement results for the pupil distance for the same user having the same head posture would vary accordingly under different measurement distances of the head to the camera. In other words, even with the same head posture, the pupil distance measurement results of the same user would still vary (quite a bit) when being configured at different measurement distances relative to the camera. Therefore, even with the same head posture, the insufficient measurement accuracy of the pupil distance obtained by the traditional manual pupillary distance (PD) measurement process caused by differences in various measuring distances of the head can be seen. Referring to FIG. 3a, a closest measurement distance from the camera of the head of the person in an illustrated image is provided, and the pupil distance is measured to be 61.4 mm. In a second actual experiment performed by inventor as shown in FIG. 3b, a normal measurement distance (at a typical or average distance) of the head of the person from the camera in the illustrated image is provided, and the pupil distance is measured to be 62.6 mm. Referring to FIG. 3c in a third actual experiment performed by inventor, a farthest measurement distance from the camera of the head of the person in the illustrated image is provided, and the pupil distance is measured to be 64.3 mm. Therefore, it is evident that at different measurement distances of the head from the camera, the pupil distance measurement results being obtained ranged between 61.4 mm to 64.3 mm, are therefore are not very precise or consistent.

Thus, the drawbacks of the traditional manual pupillary distance measurement system as exemplified by examples and usage scenarios described above are as follow: (1) there lacks a proper constrain nor guidance from an UI design for the user to take photos with a front view and place the credit card on a face region properly; (2) there lacks a proper constrain or guidance from the UI design for the user to guide him to maintain a correct head posture and a correct measurement distance during the pupil distance measurement; (3) pupillary distance measurement requires of too many manual operation steps (such as in the form of mouse cursor moving and clicking) are needed to complete the pupil distance measurement process. Therefore, the entire pupil distance measurement process is inconvenient and may be prone to produce pupil distance measurement errors. In other words, disadvantages of conventional pupillary distance (PD) measuring system include for example, being more complicated to use, providing insufficient pupillary distance (PD) measurement accuracy, and achieving unsatisfactory overall user usage experience. Therefore, there is room for improvement in the related art.

SUMMARY OF THE INVENTION

One aspect of the invention is to provide an automatic pupillary distance (PD) measurement system and corresponding measuring method with capability to automatically check to detect if a measured object moves into an adequate measuring position for pupillary distance (PD) measurement.

One aspect of the invention is to provide an automatic pupillary distance (PD) measurement system and corresponding measuring method with capability to automatically check if whether a credit card is moved into a card window or not by extracting of a black band of the credit card.

One aspect of the invention is to provide an automatic pupillary distance (PD) measurement system and corresponding measuring method with capability to automatically guide a user to move forward and/or backward for achieving a suitable measuring distance, and thereby triggering the activation of the pupillary distance (PD) measuring process/method.

One aspect of the invention is to provide an automatic pupillary distance (PD) measurement system and corresponding measuring method with capability to automatically guide the user for obtaining a correct head posture for an accurate pupillary distance (PD) measurement.

One aspect of the invention is to provide an automatic pupillary distance (PD) measurement system and corresponding measuring method with capability to automatically extract card edges of the credit card, and pupils' locations of the user, thereby capable of achieving more precise and robust PD measurement results.

One aspect of the invention is to provide an automatic pupillary distance (PD) measurement system and corresponding measuring method which gives an adequate proper guidance from an automated user interface design for the user to take photos with a front view and place the credit card on a face region properly.

One aspect of the invention is to provide an automatic pupillary distance (PD) measurement system and corresponding measuring method which gives adequate guidance from the user interface design for the user so as to guide him to maintain a correct head posture and a correct measurement distance during the pupil distance measurement.

One aspect of the invention is to provide an automatic pupillary distance (PD) measurement system and corresponding measuring method which provides a pupillary distance measurement system that requires fewer manual operation steps for measuring pupil distance.

One aspect of the invention is to provide an automatic pupillary distance (PD) measurement system and corresponding measuring method that is more convenient and more accurate to use, and offers more satisfactory overall user experience.

According to an embodiment of the present invention, an automatic pupillary distance (PD) measuring method using a camera and an user interface (UI) is provided, which includes at least the following steps: notifying a user to move his or her head position to a center of a captured face image; notifying the user to place a credit card inside a card window; notifying the user to move his or her head forward or backward to fit within a target elliptical frame, thereby maintaining a correct head posture; and obtaining a measurement of a pupil distance of the user.

According to an embodiment of the present invention, an automatic pupillary distance (PD) measuring method further includes the following steps: extracting a plurality of facial features of the captured face image of the user; showing a head current center indicator based on the facial feature extraction results; showing an elliptical frame and a target center indicator of the entire face image; calculating a first distance between the head current center indicator and the target center indicator; and determining if the first distance is below a threshold range, and if so, allowing the head current center indicator and the elliptical frame and the target center indicator to disappear from view; wherein if first distance is not below a threshold range, then allowing the head current center indicator and the elliptical frame and the target center indicator to remain in view and obtaining another captured face image; wherein the card window is obtained based on a facial tracking result, and the method further comprising of performing a credit card band detection on the credit card and determining if the entire credit card is located within the card window, and if so, allowing the card window to disappear from view; wherein if determining the entire credit card is not located within the card window, then allowing the card window to remain in view and obtaining another captured face image. The automatic PD measuring method further includes the following steps: showing an elliptical frame of a moving head of the user; showing the target elliptical frame; aligning the elliptical frame of the moving head thereof with the target elliptical frame is done by the user moving his or her head forward or backward to fit within the target elliptical frame; and determining if the elliptical frame of the moving head is aligned with the target elliptical frame, and if so, allowing the elliptical frame of the moving head to disappear from view, and allowing the target elliptical frame to disappear from view; wherein if determining that the elliptical frame of the moving head is not aligned with the target elliptical frame, then allowing the elliptical frame of the moving head and the target elliptical frame to remain in view, and to obtaining another captured face image. In the automatic PD measuring method, the first distance between the head current center indicator and the target center indicator is expressed in an equation: $Ds=|Cc-Tc|$, where $Ds$ represents the first distance, $Cc$ represents the head current center indicator, and $Tc$ represents the target center indicator.

According to an embodiment of the present invention, a method for automatically measuring pupillary distance includes the following steps: obtaining a face image of a user from a camera; extracting a plurality of facial features of the face image of the user; showing a head current center indicator based on the facial feature extraction results; showing an elliptical frame and a target center indicator of the entire face image of the user; calculating a first distance between the head current center indicator and the target center indicator; determining if the first distance is below a threshold range or not; allowing the head current center indicator to disappear from view; allowing the elliptical frame and the target center indicator to disappear from view; showing a card window based on a facial tracking result; performing a credit card band detection; determining if the entire credit card is located within the card window; allowing the card window to disappear from view; showing the elliptical frame of a moving head of the user; showing the target elliptical frame; notifying the user to align the elliptical frame of the moving head thereof with the target elliptical frame and maintaining a correct head posture; determining if the elliptical frame of the moving head is aligned with the target elliptical frame; allowing the elliptical frame of the moving head to disappear from view; allowing the target elliptical frame to disappear from view; and performing a pupillary distance (PD) measurement. In the method for automatically measuring pupillary distance, the card band detection is performed by the following steps: identifying a vertical position of the black band of the credit card; extracting left and right edges of the black band; saving as a current band; and checking to see if the current band corner points are all located inside the card window. In addition, the vertical position of the black band of the credit card is identified near center (PW) to make a reversed gray vertical profile as a V-profile and taking a maximum width band beyond average gray (Avg) as a V-band, the near center of the V-band is to make an H-profile, and two maximum edges are extracted at the left and right sides of the H-profile as being a H-band. The target center indicator indicates a location of a target center, in which the target center and the target elliptical frame are obtained by: determining a width and a height of the target elliptical frame; determining the target center by checking to see if the head is within a measurable range to set the target center as an image center; guiding the user to move his head forward or backward; calculating a center difference (sy) between a facial tracking shape and the target elliptical frame in pixels, in which a current facial tracking shape center is (curr_face_shape.cx, curr_face_shape.cy), where
Center.x=curr_face_shape.cx;
Center.y=curr_face_shape.cy−sy.

These and other aspects of the present invention will no doubt become obvious to those of ordinary skill in the art after reading the following detailed description of the preferred embodiments that is illustrated in the various figures and drawings.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIGS. 4a, 4b, 4c, 4d, and 4e and FIG. 5 together show an automatic pupillary distance (PD) measuring method which has an user interface (UI) process of an automatic pupillary distance (PD) measurement system in accordance with a first embodiment of present invention.

FIG. 12 shows the location of the card window with respect to the corresponding facial features for the second embodiment.

FIGS. 16a, 16b, and 16c show convergence or matching of the two elliptical frames of the (outer) green frame and the (inner) black frame by the user moving his face backward for allowing the measure of the pupil distance (PD).

DETAILED DESCRIPTION OF THE PREFERRED EMBODIMENTS

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1B:
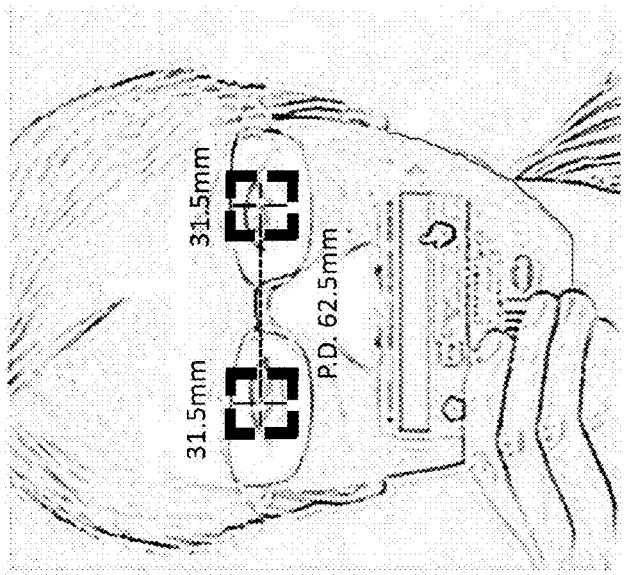
FIGS. 1a and 1b show a black band of the credit card undergoes adjustment, a pupil center undergoes adjustment, and followed by obtaining a pupillary distance value for a traditional manual visual detection and measurement system.
Figure 1A:
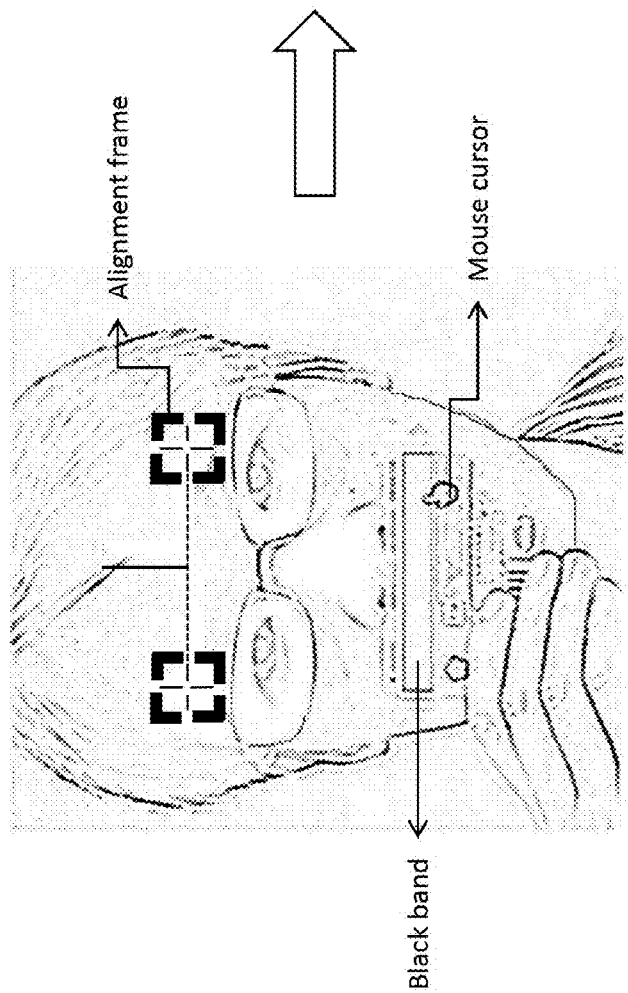
Figure 2C:
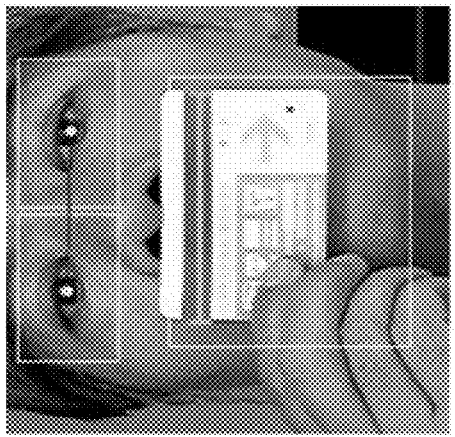
FIGS. 2a, 2b, and 2c show different pupil distance measurement results at a same measurement distance from the camera with a user having different head postures in a first usage scenario obtained by traditional manual pupillary distance measurement system.
Figure 2B:
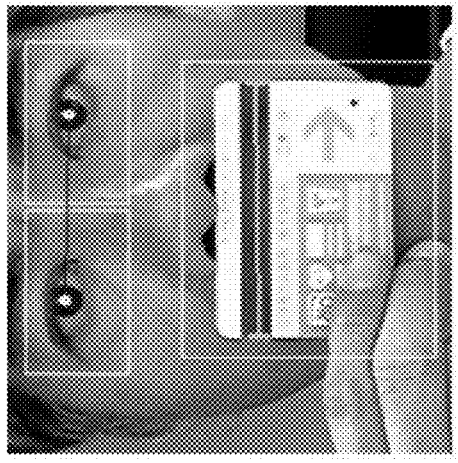
Figure 2A:
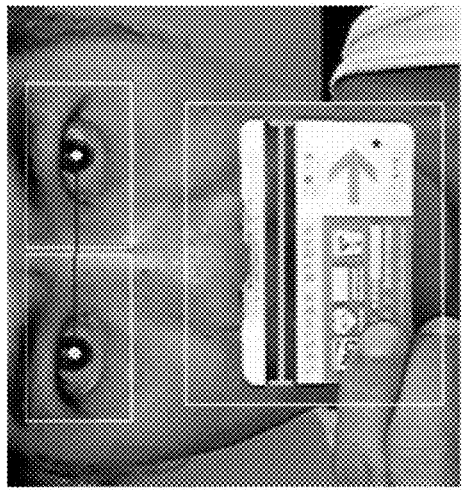
Figures 3A, 3B, 3C:
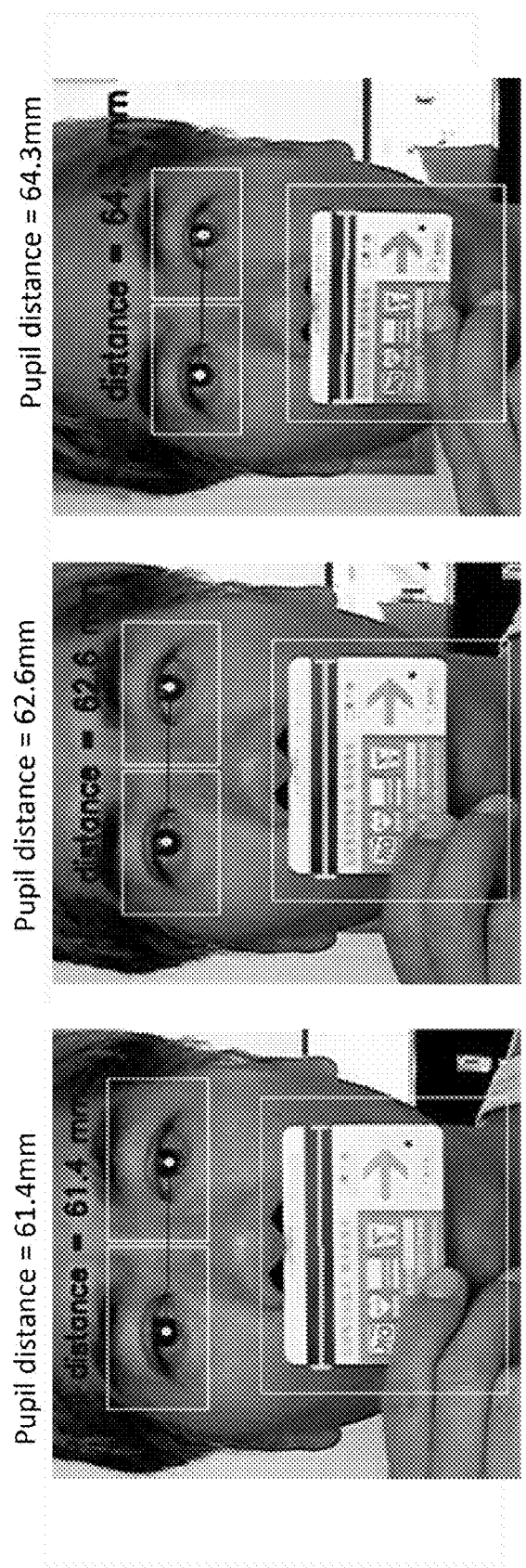
FIGS. 3a, 3b, and 3c show different pupil distance measurement results of the user having the same head posture but under different measurement distances of the head to the camera in a second usage scenario obtained by traditional manual pupillary distance measurement system.
Figure 5:
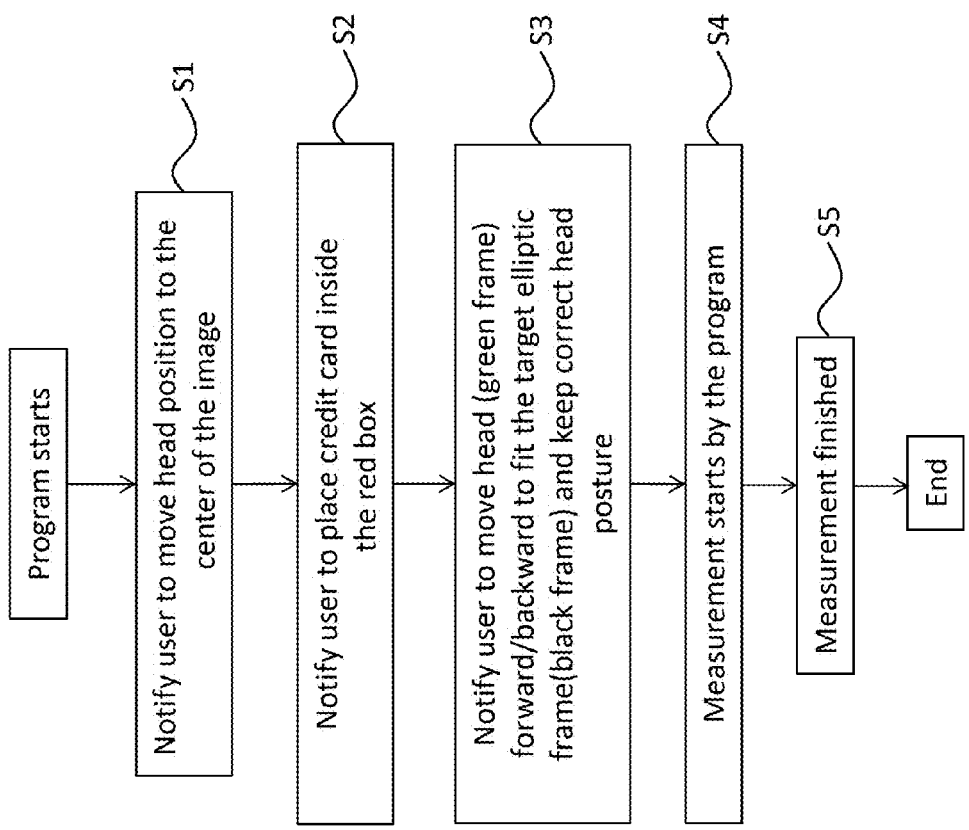

An automatic pupillary distance (PD) measurement method is described herein as follow. According to a first embodiment, as shown in FIG. 5, an automatic pupillary distance (PD) measuring method using a camera and an user interface (UI), and performed using a processor of an electronic device, is described as follow in the following steps: In Step S1, A user is notified to move his or her head position to a center of a captured image, as shown in FIG. 4a. In Step S2, The user is notified to place a credit card inside the card window, as shown in FIG. 4b. In Step S3, the user is notified to move the head (moving the green-color dash-line frame illustrated as an enclosed dash line oval) forward/backward to fit within a target elliptical frame (black-colored dash line illustrated as an enclosed dash line oval) and maintain a correct head posture as shown in FIG. 4c. In Step S4, measurement of the pupil distance is started by the program, as shown in FIG. 4d. In Step S5, measurement of the pupil distance is completed, as shown in FIG. 4e.

In the fully automatic system operation design of the automatic pupillary distance (PD) measuring method for the first embodiment of present invention, facial tracking and object tracking are utilized to form the automatic pupillary distance (PD) measuring method to build up an automatic PD measurement system. In addition, a Smart User Interface (UI) and a notified message are provided based on facial and object tracking to guide the user to easily use the automatic PD measurement system by moving his head and placing the credit card on the face region only but without requiring of performing any manual steps. Thus, there is no need to press any buttons, touch screen or to move the mouse during the entire PD measurement process of the first embodiment.

Figure 6:
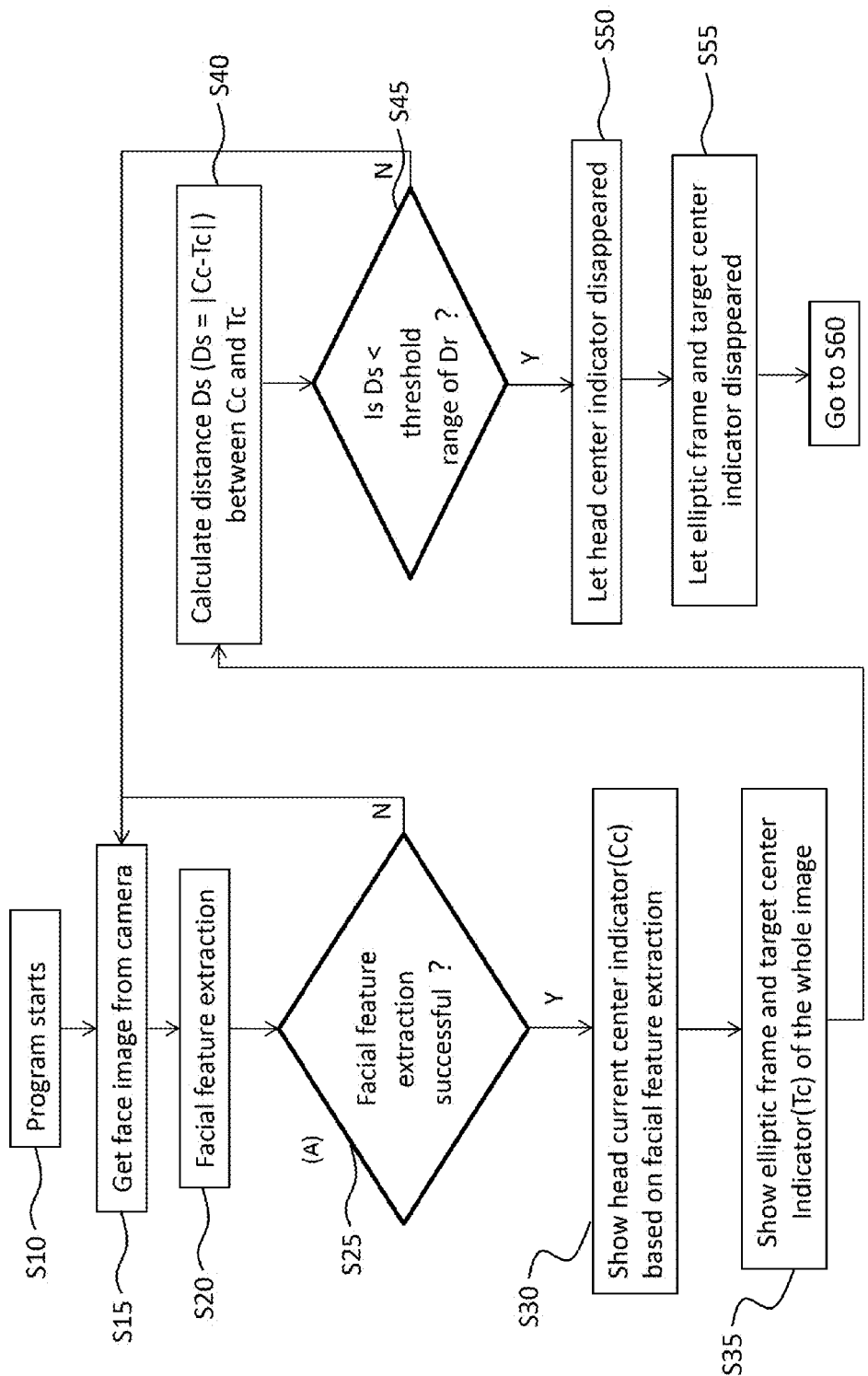
FIG. 6 show a first part of a process flow diagram of an automatic PD measuring method in accordance to a second embodiment of present invention.
Figure 7:
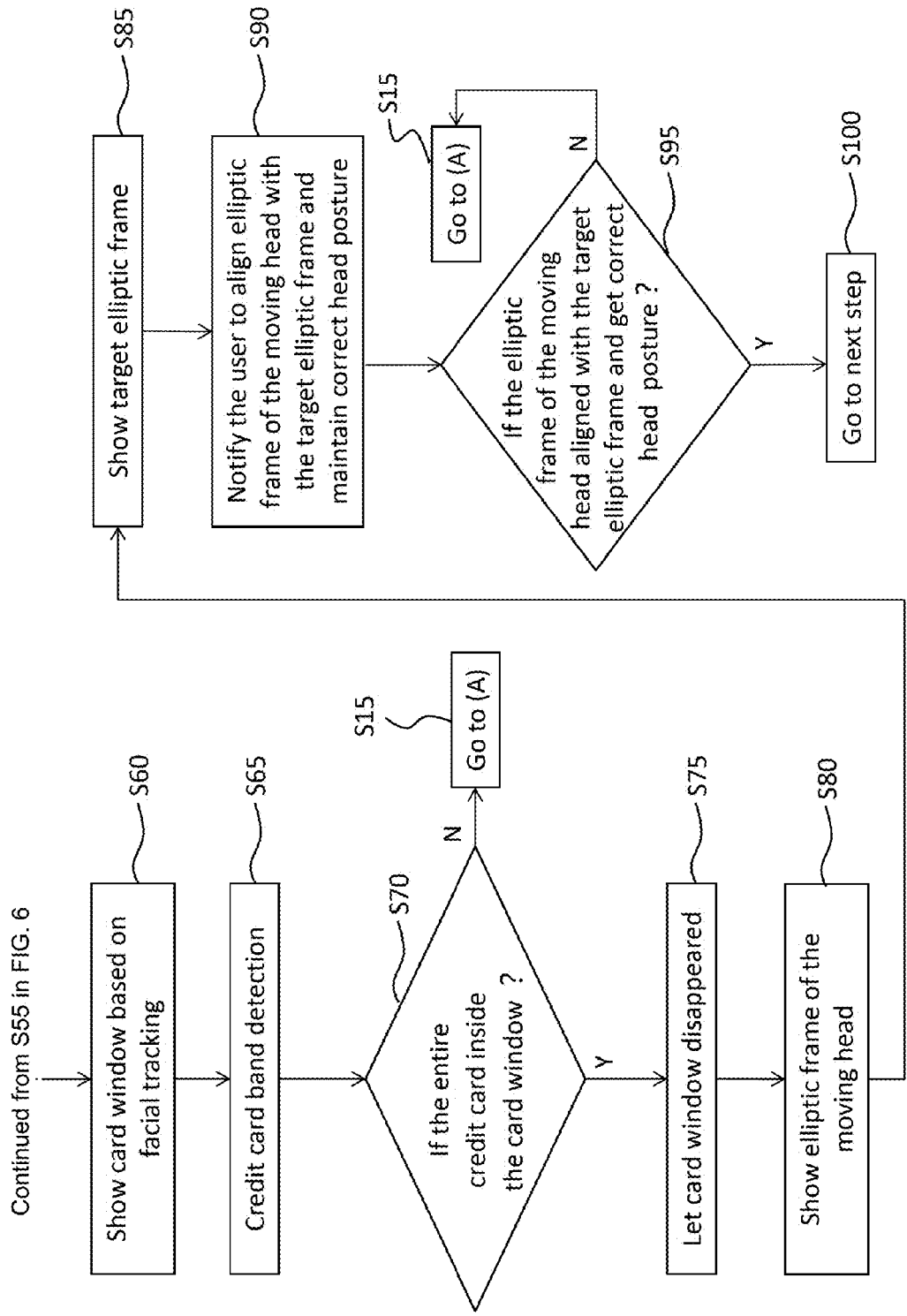
FIG. 7 shows a second part of the process flow diagram of the automatic PD measuring method in accordance to the second embodiment of present invention.
Figure 8:
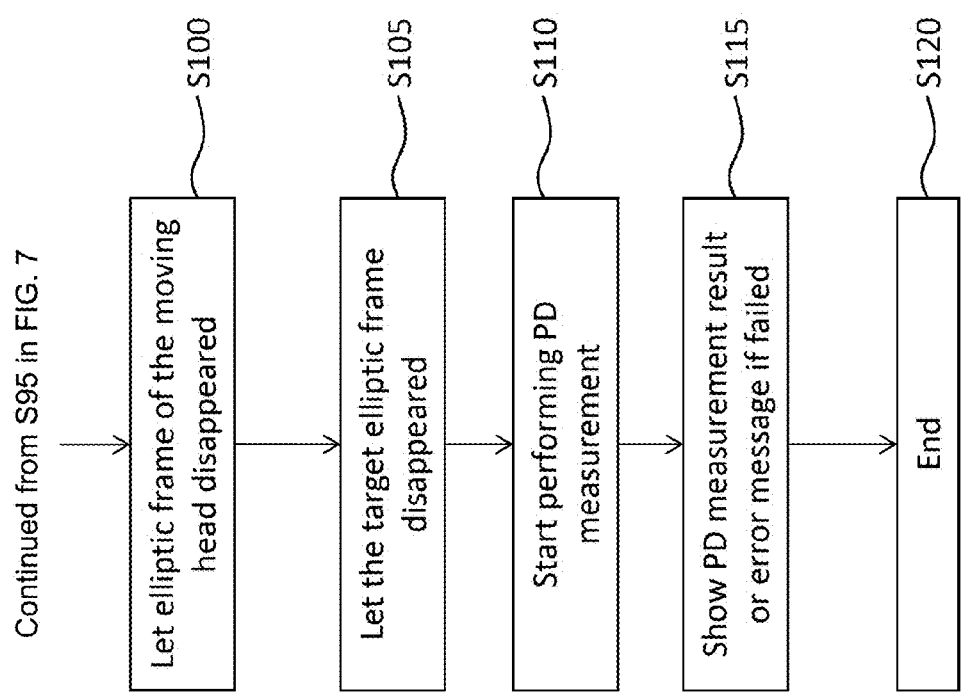
FIG. 8 shows a third part of the process flow diagram of the automatic PD measuring method in accordance to the second embodiment of present invention.

Referring to a second embodiment, an automatic PD measurement method performed using a processor of an electronic device is shown from FIG. 6 to FIG. 8, which includes the following steps: In Step S10, the PD measuring method starts. In Step S15, the face image of a user is obtained from a camera. In Step S20, the facial features of the user are extracted. In Step S25, it is determine if the facial feature extraction is successful or not, and if so, proceed to Step S30; however if not, proceed to step S15. In Step S30, a head current center indicator (Cc) based on the facial feature extraction results obtained in Step S20 is shown/displayed. In Step S35, an elliptical frame and a target center indicator (Tc) of the entire face image is shown/displayed. In Step S40, a first distance (Ds) between the head current center indicator (Cc) and the target center indicator (Tc) is calculated, in which Ds=|Cc-Tc|. In Step S45, it is determined if the first distance (Ds) is below a threshold range (Dr) or not, and if so, proceed to Step S50; however if not, proceed to Step S15. In Step S50, the head current center indicator (Cc) is allowed to disappear from view. In Step S55, the elliptical frame and the target center indicator (Tc) are allowed to disappear from view. In Step S60, a card window based on a facial tracking result is shown/displayed. In Step S65, a credit card band detection is performed. In Step S70, it is determined if the entire credit card is located within or inside the card window, and if so, proceed to Step S75, and if not, proceed to Step S15. In Step S75, the card window is allowed to disappear from view. In Step S80, the elliptical frame of the moving head is shown/displayed. In Step S85, the target elliptical frame is shown/displayed. In Step S90: the user is notified to align the elliptical frame of the moving head with the target elliptical frame and maintain a correct head posture. In Step S95, it is determined if the elliptical frame of the moving head is aligned with the target elliptical frame and has obtained the correct head posture, and if so, proceed to Step S100; however if not so, go to Step S15. In Step S100, the elliptic frame of the moving head is let or allowed to disappear from view. In Step S105, the target elliptical frame is allowed to disappear from view. In Step S110, a PD measurement is started. In Step S115, it is determined if the PD measurement result is successful, if so, the PD measurement result is shown/displayed, and if not, the error message upon failure of performing PD measurement is shown/displayed. In Step S120, the PD measurement process is ended.

Figure 9:
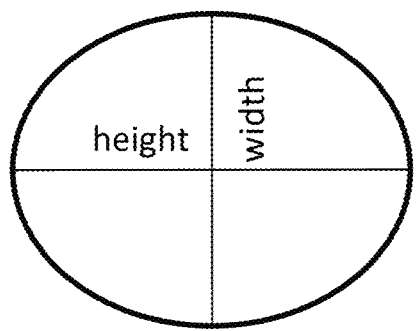
FIG. 9 shows a width and a height of the target elliptical frame according to the embodiments of present invention.

According to a third embodiment, a method of determining a target center and a target elliptical frame is provided and described in the following steps: First, referring to FIG. 9, a width and a height of the target elliptical frame is determined as follow: under a 640×480 resolution of image input, the size of the target elliptical frame is determined by experimental test (for example, using an iPhone 4s camera) at about one arm's length when holding the mobile device. The width is 208.0 pixels, and the height is 286.0 pixels. Second, the target center is determined. (a) In Step 1 as shown in FIG. 4, it is checked to see if the head is within a measurable range, just to set the target center as the image center, for example: (320, 240). (b) In Step 3 as shown in FIG. 4 also, the user is guided to move forward or backward. sy=30.0 pixels (center difference between facial tracking shape and target elliptical frame)
Center.x=curr_face_shape.cx;
Center.y=curr_face_shape.cy−sy;
where (curr_face_shape.cx, curr_face_shape.cy) is the current facial tracking shape center)

Figure 10:
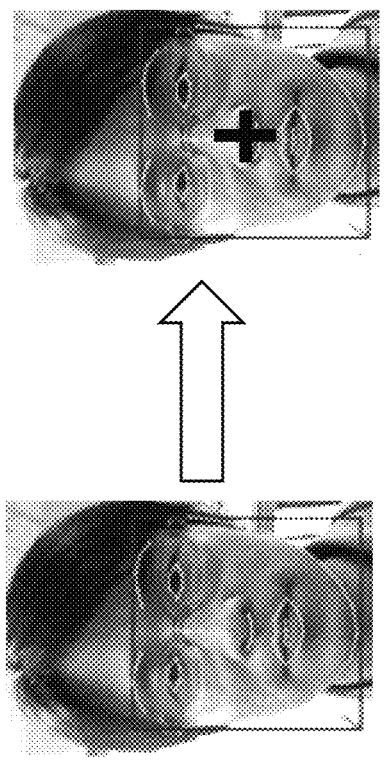
FIG. 10 shows the Head Current Center Indicator (Cc) being visible from view having a cross-shape on the face used in the second embodiment.

Referring to the second embodiment of the automatic PD measurement process as described herein above, the calculations relating to the Head Current Center Indicator (Cc) calculation are performed as follow: In Step S30, a head current center indicator (Cc) based on the facial feature extraction results is shown, as illustrated in FIG. 10. In Step S35, an elliptical frame and a target center indicator (Tc) of the entire face image is shown. In Step S40, a first distance (Ds) between the head current center indicator (Cc) and the target center indicator (Tc) is calculated, in which Ds=|Cc−Tc|. In Step S45, it is determined to see if the first distance (Ds) is below a threshold range (Dr) or not, and if so, proceed to Step S50; however if not, proceed to Step S15.

Figure 13:
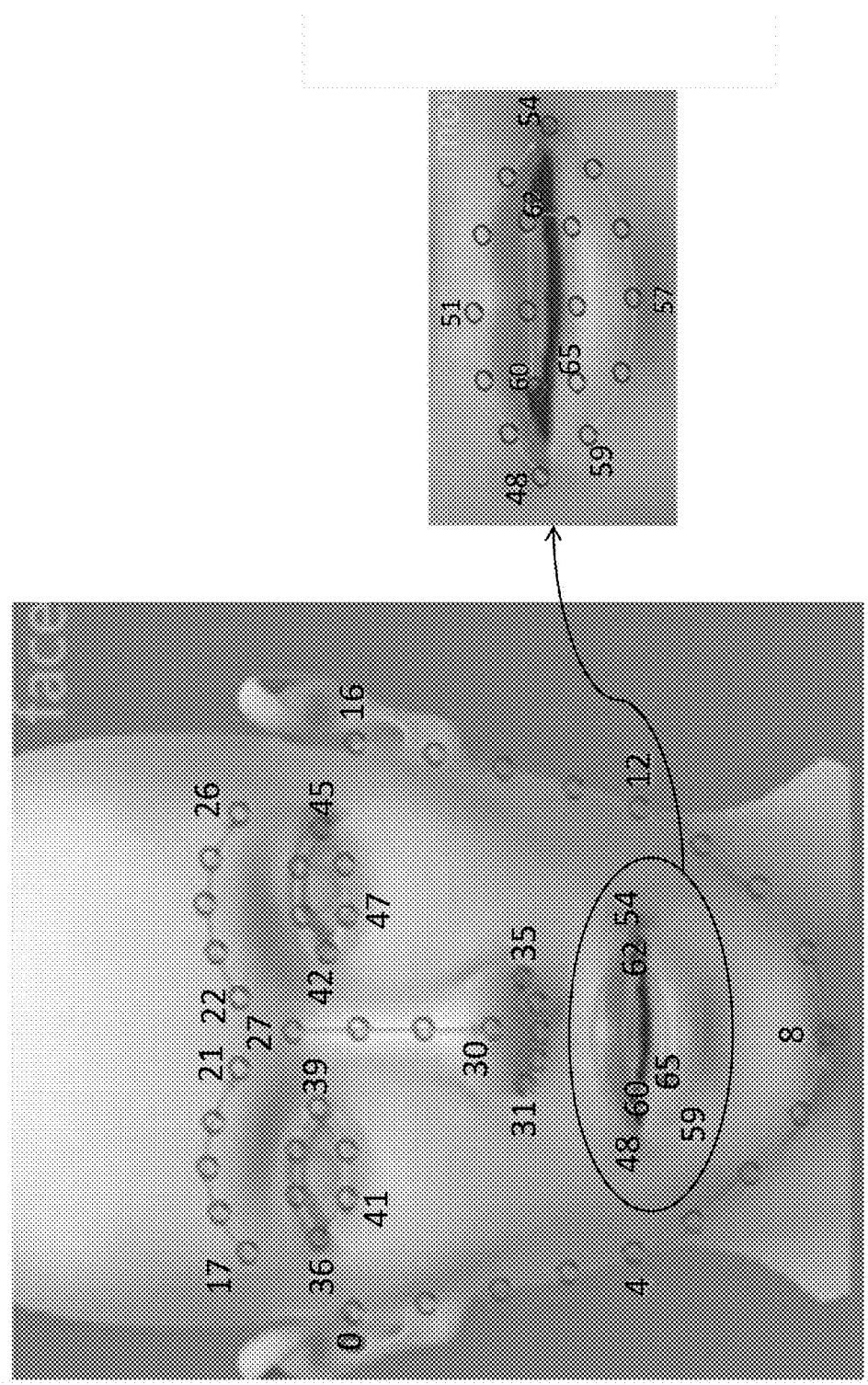
FIG. 13 shows facial feature extraction being defined as a plurality of facial tracking points by facial tracking used for a head current center indicator Cc (Ccx, Ccy) calculation.

Referring to FIG. 13, facial feature extraction can be defined as a plurality of facial tracking points (tracking points on eyebrows, eyes, nose, mouth and jaw outline . . . etc.) by facial tracking, face region by face detection . . . etc.

An example of a head current center indicator Cc (Ccx, Ccy) calculation based on 66 facial tracking points (see FIG. 13) is performed as follow using the following sets of equations:

$$Cc_x = \frac{Pt1_x + Pt2_x + \ldots Pt66_x}{66}$$

$$Cc_y = \frac{Pt1_y + Pt2_y + \ldots Pt66_y}{66}$$

Figure 11:
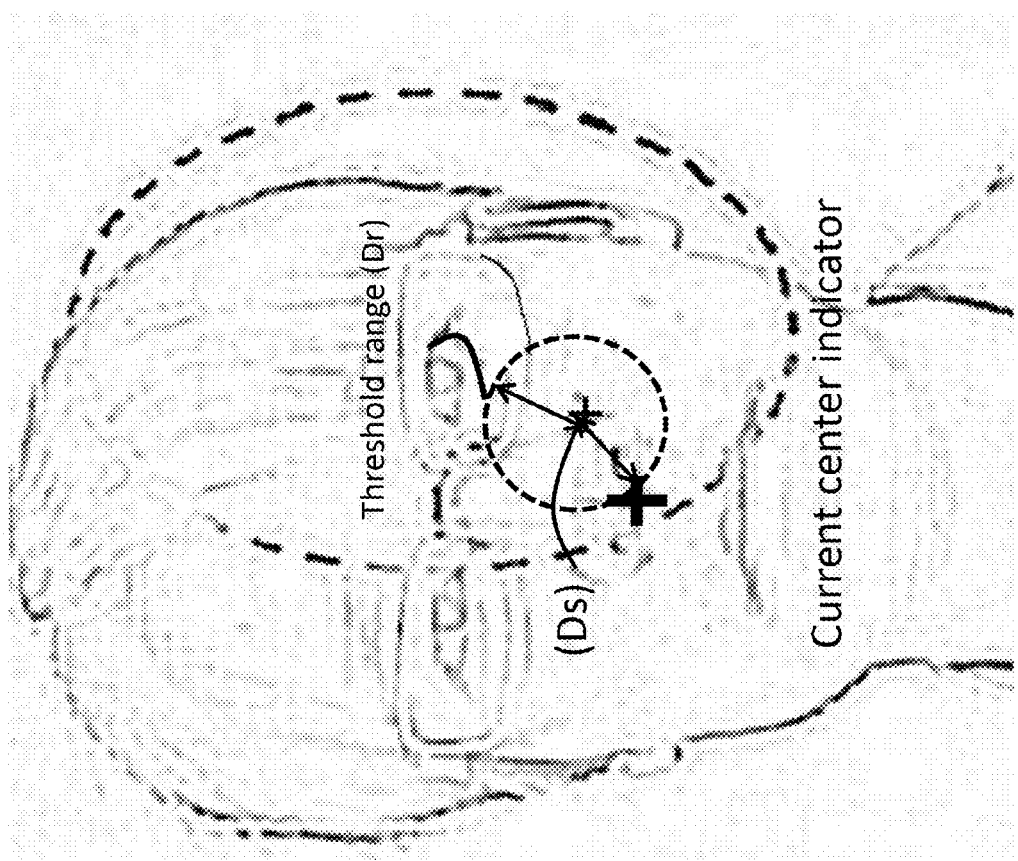
FIG. 11 shows the target shape, the head current center indicator (Cc), the first distance (Ds), and the threshold range (Dr) used in the second embodiment.

Referring to FIG. 11, the target shape, the head current center indicator (Cc), the first distance (Ds), and the threshold range (Dr) are respectively exemplified and shown therein. In the second embodiment, as shown in FIG. 6, Steps S30, S35, S40, and S45 for the first distance calculations are described below. In Step S30, a head current center indicator (Cc) based on the facial feature extraction results is shown (see FIG. 10). In Step S35, a target center indicator (Tc) and the initial target elliptical frame are shown. In Step S40, a first distance (Ds) between the head current center indicator (Cc) and the target center indicator (Tc) is calculated, in which Ds=|Cc−Tc|. In Step S45, the first distance (Ds) is determined to see if it is below a threshold range (Dr) or not.

Referring to Steps S60, S65, and S70, the credit card is determined to see if it is located within a correct range. In Step S60, a card window based on the facial tracking result is shown or becomes visible. In Step S65, a credit card band detection is performed. In Step S70, the entire credit card is determined to see if it is located inside the card window, and if so, proceed to Step S75, and if not, proceed to Step S15.

For obtaining the location values of the card windows, one or more card window calculations are performed. The following described sub-steps are performed for the card window calculations. Please refer to FIG. 13 for the notation of the facial feature points location, in which each facial feature point is identified by a sequential number, i.e. p0, p1, p2, p3, p4 . . . p65. (with many of the included facial feature points omitted herein for the sake of brevity as represented by " . . . "). In addition, FIG. 12 shows the location of the card window with respect to the corresponding facial feature points.

The card window calculations Sub-Step 1 is as follow:
Distances of the left/right eyes are calculated as follow:
Inner distance (Di) between the left/right eye inner point (feature points p39 and p42) is determined.
Outer distance (Do) between the left/right eye outer point (feature points p36 and p45) is determined.
max_x and min_x are the eye's maximum x-values and minimum x_value of coordinate points, respectively.
max_y and min_y are the eye's maximum y-values and minimum y_value of coordinate points, respectively.

The card window calculations Sub-Step 2 is as follow:
Card window's values are determined. A card window width can be calculated by the following equation:

$$\text{Card window width}=Do+0.6*Di$$

A card window height can be calculated by the following equation:

$$\text{Card window height}=(max\_y-min\_y)+3.0*Di$$

Card window start coordinates (card.x and card.y), can be expressed in the following equations, respectively:

$$card.x=p36.x-0.3*Di,$$

$$card.y=p30.y+0.4*Di$$

(where feature point p30 is at located at the nose tip)

Figure 14:
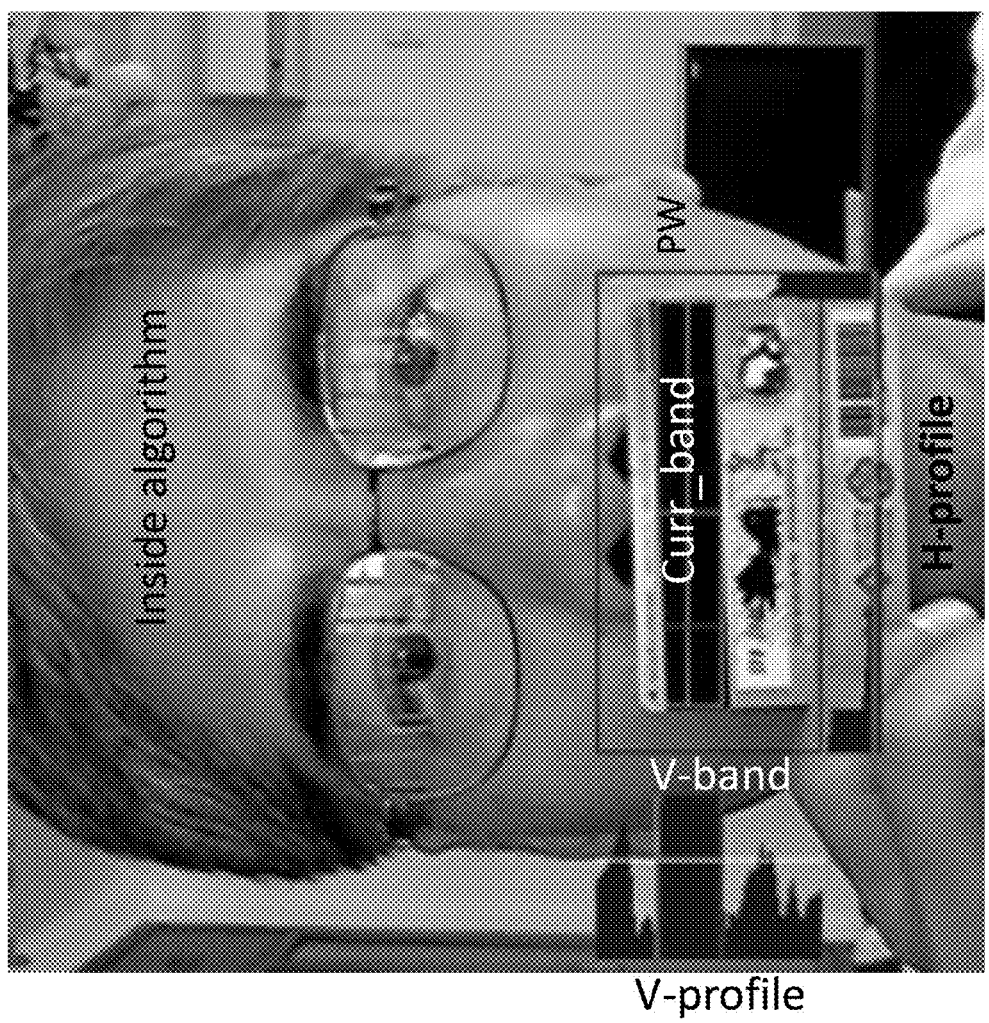
FIG. 14 shows various items and features such as vertical position and left/right edges of the black band of the credit card, V-band, V-profile, H-profile, PW, curr_band used in calculations performed on a card band of a credit card.

Referring to FIG. 14, the card band is calculated. The following sub-steps are performed for calculating the card band, and exemplified in FIG. 14 as follow: In card band calculation Sub-Step 1, a vertical position of the black band of the credit card is identified by performing the following:
  (a) Near center (PW) to make a reversed gray vertical profile (a V-profile), and
  (b) Take a maximum width band beyond an average gray (Avg) as a final result (a V-band)
In card band calculation Sub-Step 2, the left/right edges of the black band of the credit card are extracted by performing the following:
  (a) Near center of the V-band to make a horizontal profile (an H-profile)
  (b) Extract two maximum edges at left/right sides of the H-profile as being a H-band.
In card band calculation Sub-Step 3, the V-band and the H-band are saved as a "current band" (curr_band). In card band calculation Sub-Step 4, the curr_band's (current band) 4 corner points are check to see if they are all located inside the card window.

Referring to FIG. 7, Steps S80, S85, S90, and S95 are provided for aligning the elliptical frame of the moving head with the target elliptical frame to obtain the correct head posture for the user for the automatic PD measuring method in accordance with the second embodiment. In Step S80, the elliptical frame of the moving head is shown. In Step S85, the target elliptical frame is shown. In Step S90, the user is notified to align the elliptical frame of his moving head with the target elliptical frame and maintain a correct head posture. In Step S95, it is determined as to whether if the elliptical frame of the moving head of the user is aligned with the target elliptical frame and has thus obtained the correct head posture, and if so, proceed to Step S100, and if not, go to Step S15.

Figure 15:
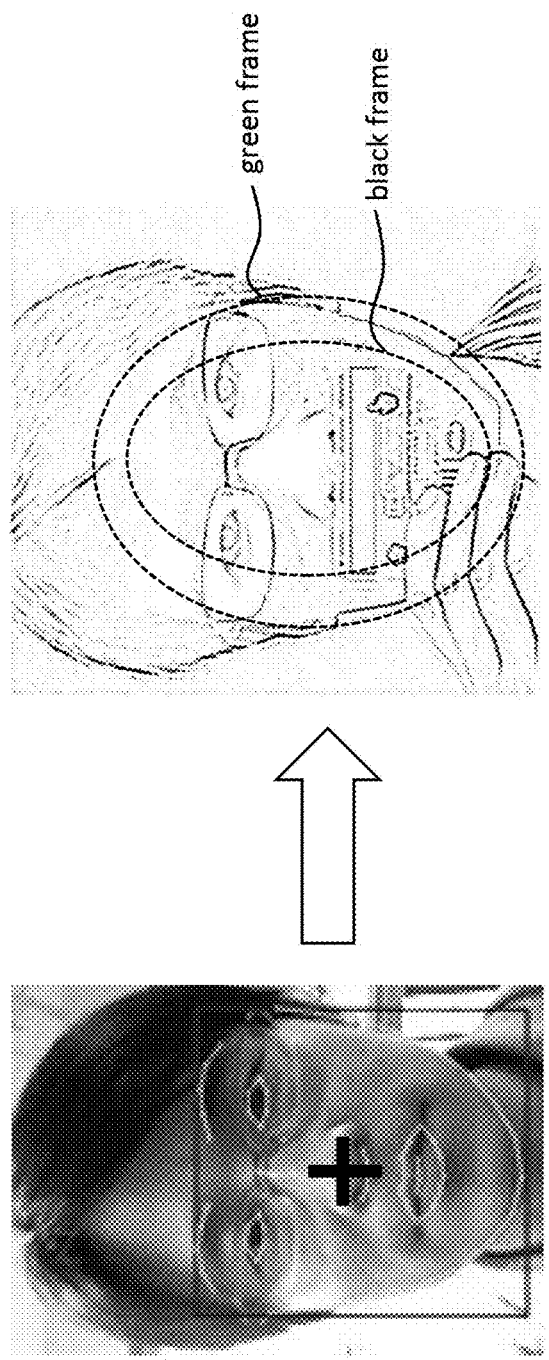
FIG. 15 shows a current center of the face and scaling information from facial tracking of the user being used to form an elliptical frame of the moving head (green frame) and a target elliptical frame (black frame).

Referring to FIG. 15, a current center of the face and scaling information from facial tracking of the user are used to draw an elliptical frame (a green frame which is shown as a larger dotted line ellipse in the illustrated embodiment) of the moving head, and configure a black frame (target elliptical frame, which is shown as a smaller dotted line ellipse in the illustrated embodiment) that is fixed at the center of the facial image while the green frame is followed by the user's face movement.

Referring to FIG. 16a, the two elliptical frames of the (outer) green frame and the (inner) black frame are not matched, therefore, the user needs to move his face backward (or forward if need be). Referring to FIG. 16b, the two elliptical frames of the (outer) green frame and the (inner) black frame are still not matched; therefore, the user needs to move his face backward a little more. Please notice that a notification in the form of "move backward" can be shown being superimposed in the facial image for indicating the user to move his head accordingly. Referring to FIG. 16c, the two elliptical frames of the green frame of the moving head and the black frame/target elliptical frame are finally matched; therefore, it is then ready to proceed to measure the pupil distance (PD).

Figures 17A, 17B, 17C:
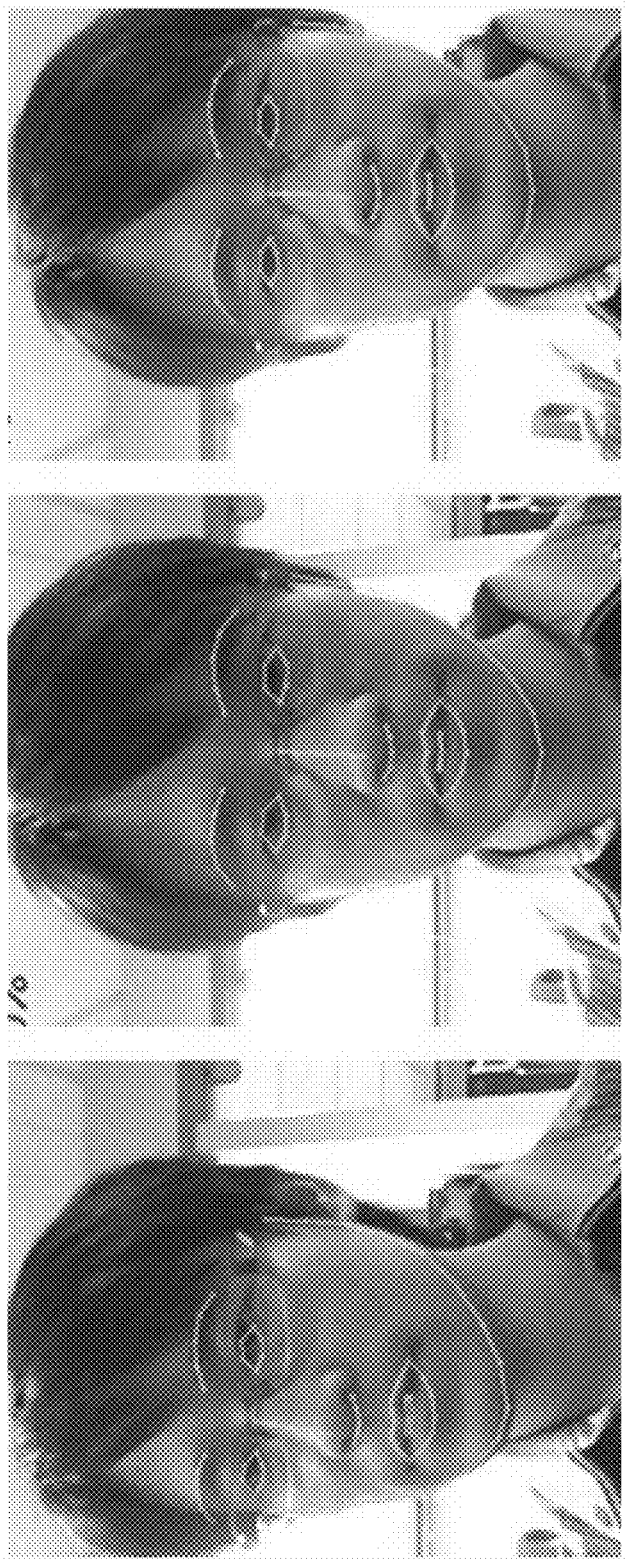
FIGS. 17a, 17b, 17c show when the pitch and yaw angles are greater than 5 degrees or the pitch angle is greater than 5 degrees, the head posture is not correct, but when the roll, pitch, and yaw angles are respectively less than 5 degrees, then the head posture is thereby configured correctly for PD measuring.

Referring to FIGS. 17a, 17b, 17c, condition of the head posture constrain is provided as follow: The roll, yaw and pitch angles of the face obtained from facial tracking should be less than some preset threshold angular values. For example: 5 degrees can be the preset threshold angular value. When the pitch and yaw angle is greater than 5 degrees, then the head posture is not correct as shown in FIG. 17a. Meanwhile, when the pitch angle is greater than 5 degrees, then the head posture is not correct as shown in FIG. 17b. Then when the roll, pitch, and yaw angles are respectively less than 5 degrees, then the head posture is thereby configured correctly for PD measuring as shown in FIG. 17c.

Figure 18:
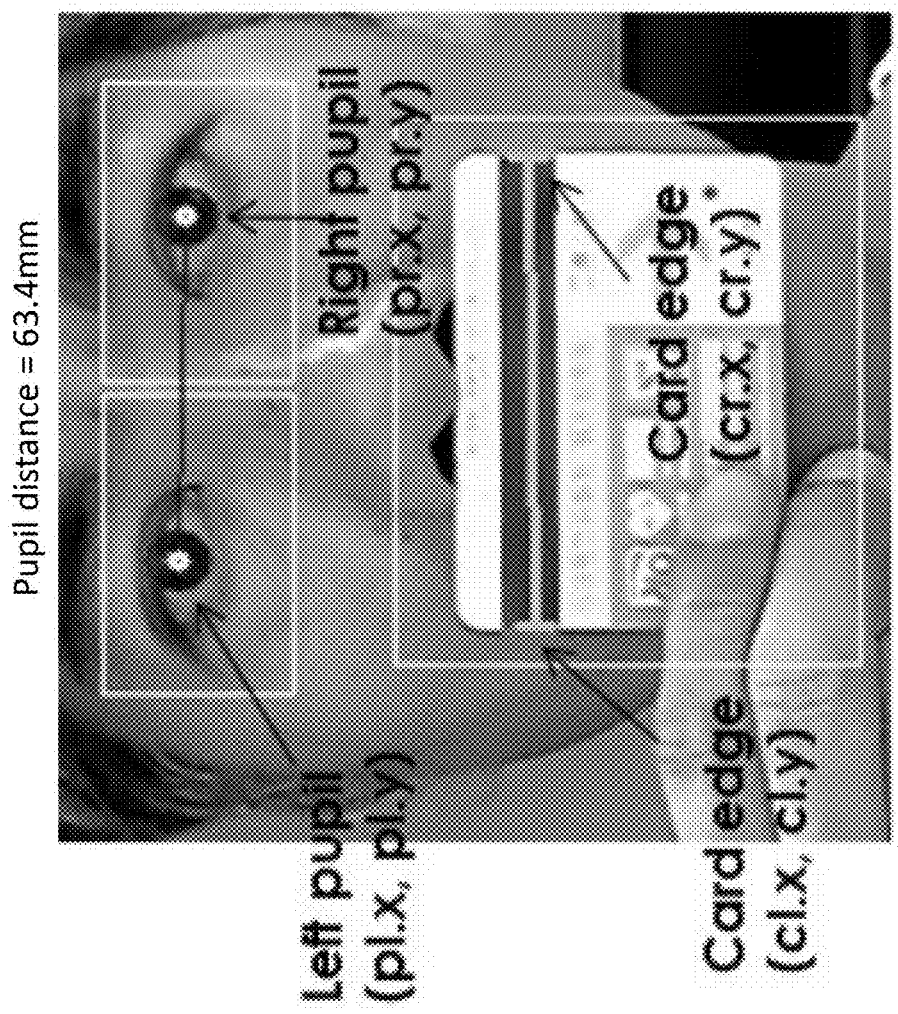
FIG. 18 shows eye locations (pl.x, pl.y) and (pr.x, pry) for the left pupil and the right pupil, credit card edge locations (cl.x, cl.y) and (cr.x, cr.y) for the left card edge and the right card edge used for extracting the pupils' locations of the user, and calculating the PD measurement value.

In Steps S110, S115, and S120 in accordance with the second embodiment, the PD measurement is performed and results are shown or displayed. In Step S110, a user is to performing a PD measurement by extracting pupils' location and finding the PD value thereof. In Step S115, it is determined whether if the PD measurement result is successful, if so, show the PD measurement result, and if not, show the error message upon failure of performing PD measurement. In Step S120, the PD measurement is ended. FIG. 18 illustrates the showing of the PD measurement. The following are the sub-steps for extracting pupils' location and finding the PD measurement value for Step S110.

In Sub-Step 1, the pupils' locations are extracted by the following:
(a) based on eyes region captured by facial tracking, and scanning that eye region to find the place which has the largest reversed gray level. To record that location, it's the pupil's location for one of the eyes. Both eyes locations are (pl.x, pl.y) and (pr.x, pr.y) for the left pupil and the right pupil, respectively;
(b) an image length between pupils 'plen' is defined as the distance between points pl and pr.

In Sub-Step 2, edge features of two sides of the black band of the credit card are extracted (a) based on curr_band's corner points to find (cl.x, cl.y) and (cr.x, cr.y); (b) by finding the image length 'clen' to be defined as the distance between points cl and cr.

In Sub-Step 3: PD is calculated, as illustrated in FIG. 18 to be 63.4 mm, by performing the following:

(a) setting a credit card standard width defined as cwidth=85.6 mm;

(b) Image resolution Ires is defined in the following equation:

Image resolution $I_{res} = cwidth/clen$ (mm/pixel)

(c) Pupillary Distance is defined in the following equation:

$PD = plen \times I_{res}$

As can be seen from the embodiments of present invention, advantages of an automatic pupillary distance (PD) measurement system which incorporates the automatic pupillary distance (PD) measuring method of the embodiments of present invention includes the following: Capability to automatically check to detect if the user's head moves into an adequate and measurable measuring position is provided. Capability to automatically check if whether the credit card is moved into a card window or not by extracting of a black band is provided. Capability to automatically guide the user to move forward/backward for achieving a suitable measuring distance is provided, and thereby trigger activation of the pupillary distance (PD) measuring process. Capability to automatically guide the user for obtaining a correct head posture for an accurate pupillary distance (PD) measurement is provided. Capability to automatically extract card edges of the credit card, and pupils' locations of the user by a proposed PD measuring method capable of achieving more precise and robust PD measurement results is also provided.

As can be seen from the embodiments of present invention, an automatic pupillary distance (PD) measurement system can be realized by adopting the automatic pupillary distance (PD) measuring method according to at least one embodiment of present invention. The automatic pupillary distance (PD) measurement system can include an electronic device having a LCD display screen, a credit card, and a front-facing camera. The electronic device can be a stand-alone electronic kiosk, a mobile smartphone, a computer, a laptop, a tablet PC, etc, but is not limited thereto. The front-facing camera can be used to capture the facial image of the user and the credit card for performing pupillary distance measuring. Meanwhile, the electronic device can include all of the software programs for performing the automatic PD measuring method can be stored in the form of app, application program, etc. . . . but is not limited thereto. In other embodiment, some or all of the software programs for performing the automatic PD measuring method can be obtained remotely via Internet, wherein the software programs for performing the automatic PD measuring method are available as web-based cloud-service.

It is believed that the present embodiments and their advantages will be understood from the foregoing description, and it will be apparent that various changes or modifications may be made thereto without departing from the spirit and scope of the disclosure or sacrificing all of its material advantages.

What is claimed is:

1. An automatic pupillary distance (PD) measuring method using a camera and an user interface (UI), wherein the measuring method is performed using a processor of an electronic device, comprising:

notifying a user to move his head position to a center of a captured face image;

generating facial tracking of the captured face image;

generating, from a determined center of the captured face image and from the facial tracking, an elliptical frame that moves and follows a moving head of the user;

notifying the user to place a credit card inside a card window and deriving a reference length from said credit card;

showing the elliptical frame of the moving head of the user over the captured face image;

showing a target elliptical frame that is fixed at a center of the captured face image;

aligning the elliptical frame of the moving head thereof with the target elliptical frame by the user moving his or her head forward or backward to fit the elliptical frame of the moving head within the target elliptical frame, thereby maintaining a correct head posture; and allowing the elliptical frame of the moving head and the target elliptical frame to disappear from view, respectively, upon determining that the elliptical frame of the moving head is aligned with the target elliptical frame; and obtaining, using said derived reference length, a measurement of a pupil distance of the user.

2. The automatic PD measuring method as claimed in claim 1, further comprising:

extracting a plurality of facial features of the captured face image of the user;

showing a head current center indicator based on the facial feature extraction results;

showing an elliptical frame and a target center indicator of the entire face image;

calculating a first distance between the head current center indicator and the target center indicator; and allowing the head current center indicator and the elliptical frame and the target center indicator to disappear from view upon determining that the first distance is below a threshold range.

3. The automatic PD measuring method as claimed in claim 2, wherein allowing the head current center indicator and the elliptical frame and the target center indicator to remain in view and obtaining another captured face image upon determining that the first distance is not below a threshold range.

4. The automatic PD measuring method as claimed in claim 2, wherein the card window is obtained based on a facial tracking result, with the method further comprising performing a credit card band detection on the credit card and allowing the card window to disappear from view upon determining that the entire credit card is located within the card window.

5. The automatic PD measuring method as claimed in claim 4, wherein when determining the entire credit card is not located within the card window, allowing the card window to remain in view and obtaining another captured face image.

6. The automatic PD measuring method as claimed in claim 1, wherein allowing the elliptical frame of the moving head and the target elliptical frame to remain in view, and obtaining another captured face image upon determining that the elliptical frame is not aligned with the target elliptical frame.

7. The automatic PD measuring method as claimed in claim 2, wherein the first distance between the head current center indicator and the target center indicator is expressed as an equation:

$$Ds=|Cc-Tc|,$$

wherein Ds represents the first distance, Cc represents the head current center indicator, and Tc represents the target center indicator (Tc).

8. A method for automatically measuring pupillary distance, wherein the method is performed using a processor of an electronic device, comprising:
   extracting a plurality of facial features of a face image of a user;
   showing, over the face image of the user, a head current center indicator, an elliptical frame that moves and follows a moving head of the user, and a target center indicator;
   calculating a first distance between the head current center indicator and the target center indicator;
   allowing the head current center indicator, the elliptical frame and the target center indicator to disappear from view upon determining that the first distance is below a threshold range;
   showing a credit card window, having the user position a credit card within the credit card window and performing a credit card band detection to derive a reference length from said credit card;
   showing, over the face image of the user, the elliptical frame of the moving head of the user and a target elliptical frame that is fixed at a center of the face image of the user;
   notifying the user to align the elliptical frame of the moving head with the target elliptical frame and to maintain a correct head posture;
   allowing the elliptical frame of the moving head and the target elliptical frame to disappear from view upon determining that the elliptical frame of the moving head is aligned with the target elliptical frame; and
   performing, using said derived reference length, a pupillary distance (PD) measurement.

9. The method for automatically measuring pupillary distance of claim 8, after the step of performing the credit card band detection, further comprising:
   allowing the credit card window to disappear from view upon determining that the entire credit card is located within the credit card window.

10. The method for automatically measuring pupillary distance of claim 8, wherein the head current center indicator is displayed based on the facial feature extraction results.

11. The method for automatically measuring pupillary distance of claim 8, wherein the credit card window is displayed based on a facial tracking result.

12. The method for automatically measuring pupillary distance of claim 8, wherein the credit card band detection is performed by:
   identifying a vertical position of a black band of the credit card;
   extracting left and right edges of the black band;
   saving as a current band; and
   checking to see if the current band corner points are all located inside the credit card window.

13. The method for automatically measuring pupillary distance of claim 12, wherein the vertical position of the black band of the credit card is identified near center to make a reversed gray vertical profile as a V-profile and taking a maximum width band beyond an average gray (Avg) as a V-band, the near center of the V-band is to make an H-profile, and two maximum edges are extracted at the left and right sides of the H-profile as being a H-band.

14. The method for automatically measuring pupillary distance of claim 13, wherein the target center indicator indicates a location of a target center, the target center and the target elliptical frame are obtained by:
   determining a width and a height of the target elliptical frame;
   determining the target center by checking to see if the head is within a measurable range to set the target center as an image center;
   guiding the user to move his head forward or backward;
   calculating a center difference (sy) between a facial tracking shape and the target elliptical frame in pixels, wherein a current facial tracking shape center is (curr_face_shape.cx, curr_face_shape.cy), where
   Center.x=curr_face_shape.cx;
   Center.y=curr_face_shape.cy−sy.

15. The method for automatically measuring pupillary distance of claim 8, wherein the head current center indicator (Cc) is expressed in (Ccx, Ccy), and calculated based on 66 facial tracking points:

$$Cc_x = \frac{Pt1_x + Pt2_x + \ldots Pt66_x}{66}$$

$$Cc_y = \frac{Pt1_y + Pt2_y + \ldots Pt66_y}{66}$$

wherein Pt1 to Pt66 represents each of the 66 facial tracking points.

16. The method for automatically measuring pupillary distance of claim 8, wherein a location of the credit card window with respect to the corresponding facial features is determined by:
   calculating an inner distance (Di) between the left and right eye inner point and an outer distance (Do) between the left and right eye outer point;
   determining the eye's maximum x-values (max_x) and minimum x_value (min_x) of coordinate points, the eye's maximum y-values (max_y) and minimum y_value (min_y) of coordinate points, respectively;
   determining a location value of the credit card window by performing steps of:
   calculating a card window width by a first equation:

card window width=$Do+0.6*Di$  [1]

calculating a card window height by a second equation:

card window height=$(max\text{-}y-min\text{-}y)+3.0*Di$  [2]

wherein a plurality of card window start coordinates, card.x and card.y, are expressed in third and fourth equations, respectively:

card.x=$p36.x-0.3*Di$,  [3]

card.y=$p30.y+0.4*Di$  [4]

where the feature point p36 is located at the outer point of the left eye and where the feature point p30 is at located at the nose tip of the user.

17. The method for automatically measuring pupillary distance of claim 8, further comprising:
   showing the PD measurement after extracting the pupils' locations based on an eye region captured by facial tracking, and scanning that eye region to find the place which has the largest reversed gray level, the pupil's locations are (pl.x, pl.y) and (pr.x, pr.y) for the left pupil and the right pupil, respectively; an image length between pupils (plen) is defined as the distance between points pl and pr;

extracting edge features of two sides of a black band of the credit card based on corner points to find (cl.x, cl.y) and (cr.x, cr.y) by finding the image length (clen) to be defined as the distance between points cl and cr;

calculating the pupillary distance (PD) by setting a credit card standard width (cwidth) to be 85.6 mm, and defining an image resolution (Tres) in an equation:

$$\text{image resolution } (Tres) = c\text{width}/c\text{len in units of mm/pixels} \quad [5]$$

and defining pupillary distance (PD) in an equation:

$$PD = plen \times Tres \quad [6].$$

18. An automatic pupillary distance (PD) measurement system, comprising:

an electronic device having a LCD display screen and a front-facing camera, wherein the electronic device is configured to perform a pupillary distance (PD) measurement using the front-facing camera and an user interface (UI), comprising the steps of:

obtaining a face image of the user from the front-facing camera and extracting a plurality of facial features of the face image of an user;

displaying, over the face image of the user, a head current center indicator, an elliptical frame that moves and follows a moving head of the user, and a target center indicator of the entire face image of the user;

calculating a first distance between the head current center indicator and the target center indicator;

allowing the head current center indicator, the elliptical frame and the target center indicator to disappear from view, respectively upon determining that the first distance is below a threshold range;

displaying a credit card window, having the user position a credit card within the credit card window and performing a credit card band detection to derive a reference length from said credit card, and allowing the credit card window to disappear from view upon determining that the entire credit card is located within the credit card window;

displaying, over the face image of the user, the elliptical frame of the moving head of the user and a target elliptical frame that is fixed at a center of the face image of the user, respectively;

notifying the user to align the elliptical frame of the moving head with the target elliptical frame and maintaining a correct head posture;

allowing the elliptical frame of the moving head and the target elliptical frame to disappear from view upon determining that the elliptical frame of the moving head is aligned with the target elliptical frame; and performing, using said derived reference length, the pupillary distance (PD) measurement.

19. The automatic pupillary distance (PD) measurement system of claim 18, wherein the pupillary distance (PD) measurement is displayed; the head current center indicator is displayed based on the facial feature extraction results, the credit card window is displayed based on a facial tracking result; the electronic device is a stand-alone electronic kiosk, a mobile smartphone, a computer, a laptop, or a tablet PC.

* * * * *